United States Patent [19]

Kopans

[11] Patent Number: 5,057,085
[45] Date of Patent: Oct. 15, 1991

[54] STABILIZED ASPIRATION BIOPSY NEEDLE ASSEMBLY

[75] Inventor: Daniel B. Kopans, Waban, Mass.

[73] Assignee: Medical Device Technologies, Inc., Gainesville, Fla.

[21] Appl. No.: 441,079

[22] Filed: Nov. 24, 1989

[51] Int. Cl.$^5$ .............................................. A61M 5/00
[52] U.S. Cl. .................................. 604/173; 604/158; 604/164
[58] Field of Search ...................... 604/158, 164, 173; 128/749, 751, 752, 753, 754

[56] References Cited

U.S. PATENT DOCUMENTS

| | | | |
|---|---|---|---|
| 4,776,346 | 10/1988 | Beraha et al. | 128/754 |
| 4,832,044 | 5/1989 | Garg | 128/754 |
| 4,846,799 | 7/1989 | Tanaka et al. | 604/158 |
| 4,850,373 | 7/1989 | Zatloukal et al. | 128/749 |
| 4,869,717 | 9/1989 | Adair | 604/164 |

Primary Examiner—Richard J. Apley
Assistant Examiner—Lynne A. Reichard
Attorney, Agent, or Firm—Emrich & Dithmar

[57] ABSTRACT

A stabilized aspiration biopsy needle assembly includes an introducing needle adapted to be inserted percutaneously into a human or veterinary body and advanced to the target tissue, an elongated, generally trough-shaped trocar member adapted for assembly with the introducing needle and having its distal tip extending beyond the distal tip of the introducing needle to stabilize the distal end of the introducing needle while maintaining a lumen during subsequent introduction of an aspiration needle through the introducing needle, and manipulation of the aspiration needle during aspiration procedures.

19 Claims, 2 Drawing Sheets

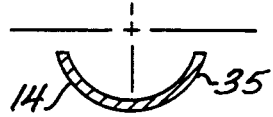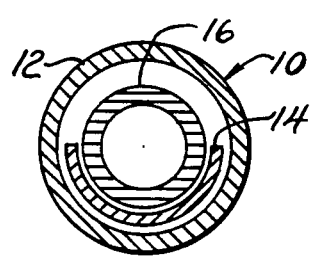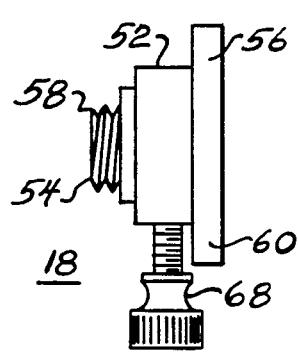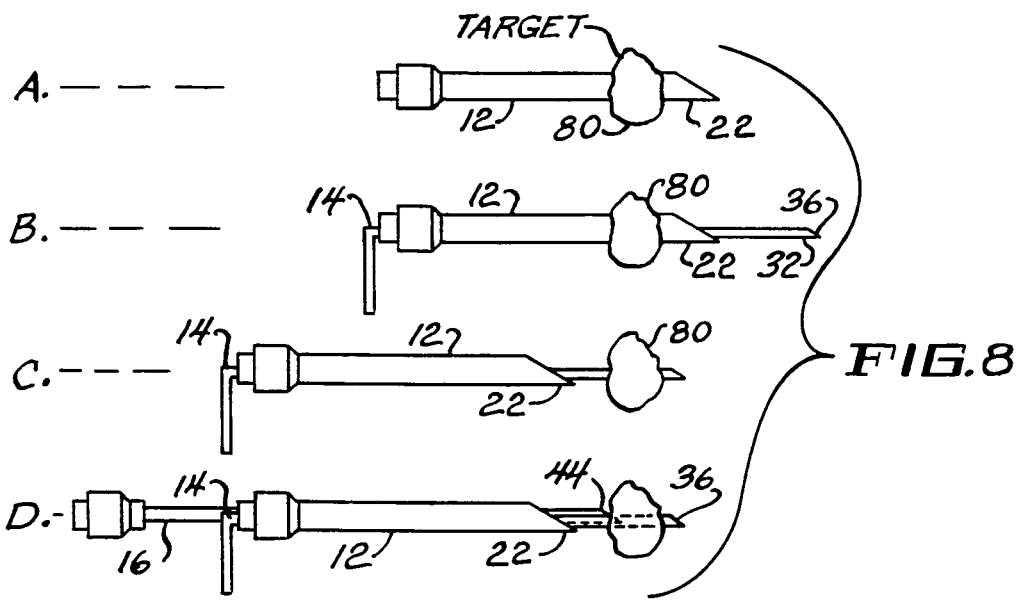

STABILIZED ASPIRATION BIOPSY NEEDLE ASSEMBLY

BACKGROUND OF THE INVENTION

The present invention relates to medical and surgical instruments, and more particularly to a stabilized aspiration biopsy needle assembly.

Aspiration biopsy needle assemblies are used in preoperative diagnostic procedures to obtain samples of body fluids and/or tissues for analysis as a means of locating and identifying cancerous and non-cancerous non-palpable lesions, for example. Such assemblies may be used in fine needle aspiration biopsy (FNAB) procedures or in soft tissue biopsy procedures. In accordance with existing practices, an introducing needle is inserted percutaneously into the body in the proximity of the target area and advanced to a target area or tissue. After the introducing needle has been properly positioned, its location is optimally confirmed by using X-ray, ultrasound, or other imaging methods. Then, an aspiration needle is advanced through the introducing needle to the target area. Generally, the aspiration needle is moved, in short strokes, in and out, to agitate the target area thereby releasing fluid samples or cellular material to be aspirated for testing. During such a procedure, the locator needle may be moved inadvertently out of the target tissue.

Thus, one problem with known procedures is that the distal end of the introducing needle may be moved out of alignment with the target tissue during agitation of the target area because no stabilization is provided for preventing withdrawal or deflection of the introducing needle completely out of the target area. Another disadvantage is that should it be desireable to re-advance the introducing needle back through the target area or lesion as in the placement of preoperative guides to direct the surgeon to the target area, it may be necessary to repeat the initial location procedures.

It would be desireable to have an aspiration biopsy needle assemble including an introducing needle which, once introduced into target tissue, will be maintained aligned with the target tissue even with movement of the needle assembly relative to the target tissue.

SUMMARY OF THE INVENTION

It is an object of the invention to provide an improved aspiration biopsy needle assembly.

Another object of the invention is to provide a movement stabilized aspiration biopsy needle assembly.

Another object of the invention is to provide a biopsy needle assembly of the type including an introducing needle and an aspiration biopsy needle wherein in use, the introducing needle is maintained in alignment with target tissue.

Further object of the invention is to provide an aspiration biopsy needle assembly of the type including an introducing needle and an aspiration needle and which includes guide means for maintaining the introducing needle in alignment with target tissue while permitting advancement and retraction of the introducing needle relative to the target tissue in use.

These and other objects of the invention are provided by the present invention which provides a method for locating and positioning an aspiration biopsy needle in a target area within a human or veterinary body, comprising inserting an introducing needle percutaneously into the body and advancing the introducing needle to the target area; advancing a trocar member through the introducing needle until its distal end extends beyond the distal end of the introducing needle and at least into the target area to provide a coaxial unit, and advancing an aspiration needle along side the trocar member and through the introducing needle to the target area with said trocar member guiding said aspiration needle to the target area.

Further in accordance with the present invention, there is provided an aspiration biopsy needle assembly for use in performing aspiration biopsy procedures at a target area within a human or veterinary body, which comprises an introducing needle having a proximal end and a distal end adapted for introduction percutaneously into the body and to be advanced therewithin to the target area; a trocar member having a proximal end and a distal end and adapted for insertion through said introducing needle until its distal end extends beyond the distal end of said introducing needle and at least into the target area to provide a coaxial unit with said distal tip of said trocar member within said target area; securing means for securing said trocar member to said introducing needle whereby said trocar member stabilizes the distal tip of the introducing needle against lateral movement relative to the target area, and an aspiration needle adapted for insertion along side said trocar member and through said introducing needle to the target area with said trocar member guiding said aspiration needle to the target area.

The invention consists of certain novel features and structural details hereinafter fully described, illustrated in the accompanying drawings, and particularly pointed out in the appended claims, it being understood that various changes in the details may be made without departing from the spirit, or sacrificing any of the advantages of the present invention.

DESCRIPTION OF THE DRAWINGS

For the purpose of facilitating and understanding the invention, there is illustrated in the accompanying drawings a preferred embodiment thereof, from an inspection of which, when considered in connection with the following description, the invention, its construction and operation, and many of its advantages will be readily understood and appreciated.

FIG. 5 is an enlarged sectional view taken along the lines 5—5 of FIG. 3;

FIG. 6 is an enlarged sectional view taken along the lines 6—6 of FIG. 1;

FIG. 7 is an enlarged view of a locking disc of the aspiration biopsy needle assembly; and, FIG. 8 illustrates the method in which the aspiration biopsy needle assembly of the present invention is used.

DESCRIPTION OF A PREFERRED EMBODIMENT

Figure 1:
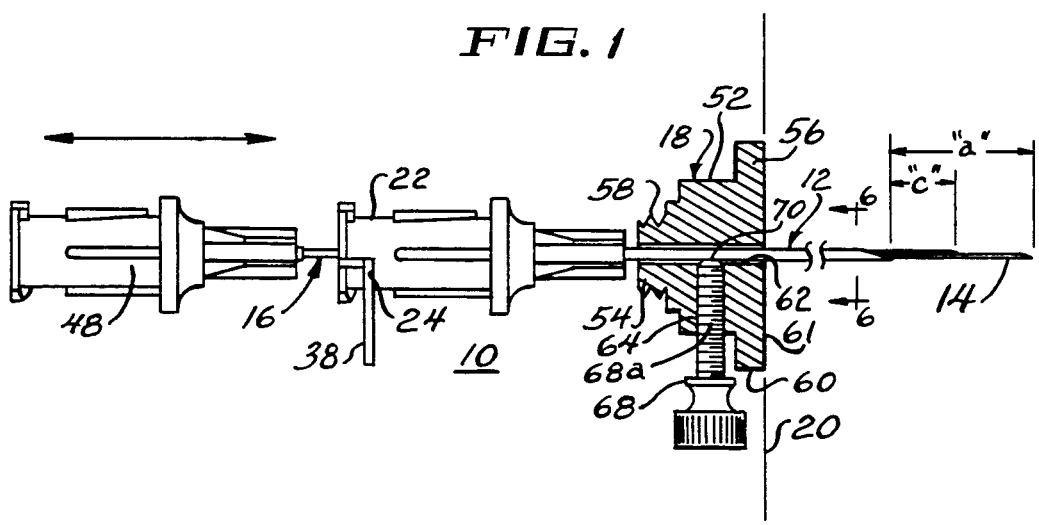
FIG. 1 is a side view of an aspiration biopsy needle assembly provided in accordance with the present invention.

Referring to the drawings, FIG. 1 illustrates the stabilized aspiration biopsy needle assembly 10 provided by the present invention. The needle assembly 10 includes an introducing needle 12, a trocar member 14, an aspiration biopsy needle 16, and a locking disc 18. The trocar member of the stabilized aspiration biopsy needle assembly 10 is used to maintain the introducing needle 12 in direct line with a target tissue that is to be aspirated using a aspiration biopsy needle which is introduced coaxially into the introducing needle and advanced to the target area through the introducing needle 12.

The needle assembly 10 of the present invention has particular application in locating cancerous non-palpable lesions in the human breast, but may be used in aspiration biopsy procedures or any medical procedure for human or veterinary bodies which requires aspiration biopsy of fluids and/or cells of a lesion, foreign body or normal structure within the body or organs of the human or veterinary body.

Figure 2:
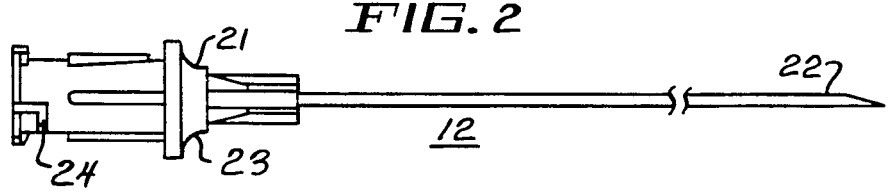
FIG. 2 is a side view of an introducing needle of the aspiration biopsy needle assembly provided by the present invention.

Referring to FIG. 2, the introducing needle 12 is a hollow thin wall 20 gauge needle having a proximal end 21 and a distal end 22. The distal end 22 of the introducing needle 12 has an a bevelled sharp pointed tip (26. The needle is preferably made of surgical steel and of a length that may vary as a function of application and for example, may be approximately 10 centimeters. The introducing needle 12 has a hub or handle 23 on its proximal end 21 to facilitate positioning of the needle in use. The hub 23 has an L-shaped slot 24 which cooperates with the trocar member 14 for securing the trocar member 14 to the introducing needle 12 as will be shown.

Figure 3:
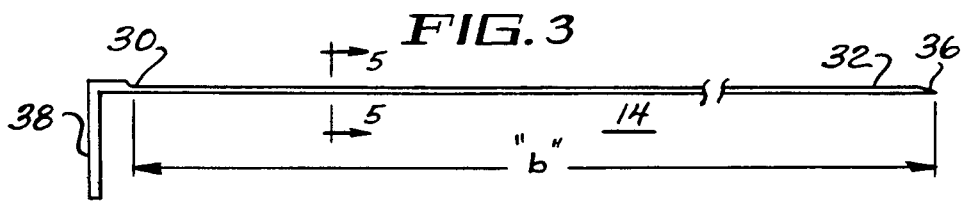
FIG. 3 is a side view of a trocar member of the aspiration biopsy needle assembly provided by the present invention.

Referring to FIG. 3, the trocar member 14 is made from a 22-gauge needle or cannula, which may be 12 centimeters in length. The length may vary as a function of application, but the trocar member 14 is greater in length than the introducing needle 12, and is preferably about 1 to 2 centimeters longer as represented by dimension "a" in FIG. 1. The trocar member 14 is composed of a rigid material such as surgical steel, polymer, or a combination thereof. The trocar member 14 has a proximal end 30 and a distal end 32 with a shank portion 33 having a generally semi-circular cross-section as illustrated in FIG. 5, over a portion "b" of its axial length, which extends from a point 34 near its proximal end 30 to its tip 36, defining an open upper portion or trough. In the exemplary embodiment, the outer surface of the trocar member is designed to fit the inner diameter of the introducing needle to maximize the residual lumen of the combined unit although other configurations may be desired for each specific application. The cross section of the annular extent 35 (FIG. 5) may vary, but a desireable range is 40% to 35% of a complete circle. Although the introducing needle and the trocar member are illustrated as being circular and semi-circular in cross-section, other cross sections of the various members could be used, including oval, triangular, etc.

The proximal end 30 has a depending portion 38 extending perpendicular to the axis of the shank portion 33 of the trocar member, defining a handle for the trocar member 14. The depending portion 38 may be formed integrally with the shank portion 33 or attached thereto in suitable manner. The distal tip 36 of the trocar member may be pointed or shovel-shaped, or blunt depending upon the application.

Figure 4:
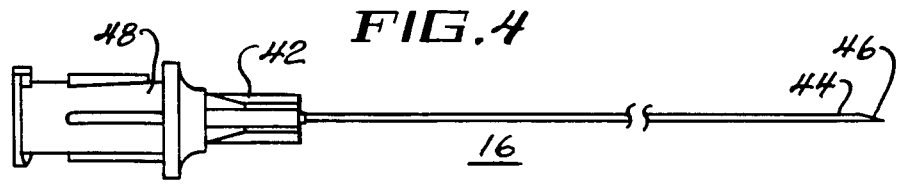
FIG. 4 is a side view of an aspiration needle of the aspiration biopsy needle assembly provided by the present invention.

Referring to FIG. 4, the aspiration needle 16 is a conventional 23 gauge needle having a proximal end 42 and a distal end 44 provided with a surgical tip 46, such as a Chiba or Green tip, although its diameter may vary with the application. The aspiration needle is made of a rigid material such as surgical steel. The aspiration needle 16 has a hub 48 on its proximal end 42 to facilitate placement and manipulation of the aspirating needle 16 in use. The aspiration needle 16 is longer than the introducing needle, but shorter than the trocar 14, and may be about 1 centimeter longer than the introducing needle 12 as represented by dimension "c" in FIG. 1.

Referring to FIGS. 1-4, the trocar member 14 is adapted to be inserted into the hollow introducing needle 12 and advanced therethrough until its distal tip portion 32 extends beyond the distal tip portion 22 of the introducing needle 12. When so positioned, the handle portion 38 of the trocar member 14 can be aligned with the groove 24 and advanced therethrough. Then the trocar member 14 is rotated clockwise, as viewed in FIG. 1, downwardly to the position illustrated in FIG. 1, securing the trocar member 14 to the introducing needle 12. When so secured together, the introducing needle 12 and the trocar member 14 assembled therewith can be moved as a unit.

The aspiration needle 16 is adapted to be advanced along the thus assembled members, along side the trocar member 14 and through introducing needle 12. As will be shown, in use, the trocar member 14 stabilizes the distal end of the needle assembly 10, thereby maintaining the introducing needle 12 in direct line with a target tissue that is to be aspirated.

The semi-cylindrical configuration of the trocar member 14 permits passage of the aspiration needle 16 along side, (FIG. 6) coaxially, for tissue sampling procedures. In use, the trocar member 14 maintains the distal end of the introducing needle in line with the target tissue even if the introducing needle is withdrawn completely out of the target tissue, and particularly during manipulation of the aspiration needle in agitating the target tissue. By keeping the introducing needle aligned with the tissue sample, coaxial needle sampling, that is cytologic aspiration or needle biopsy, will permit the reintroduction of the introducing needle 12 back through the target tissue to permit such functions as the preoperative localization of non-palpable lesions.

Referring to FIGS. 1 and 7, the stabilized aspiration biopsy needle assembly 10 further includes a locking disc 18 for providing additional support and/or stabilization for the needle assembly 10 at the point at which the needle assembly enters the body, represented by line 20 in FIG. 1. The locking disc 18 has a generally cylindrical body portion 52 with a proximal end 54 and a distal end 56. The proximal end is stepped down defining reduced diameter portion 58 adjacent to the proximal end of the introducing needle 12. The distal end 56 has an annular flange 60 which defines a relatively large contact surface 61 which engages the skin at the outer surface of the body. The locking disc 52 has an axial bore 62 extending from its proximal end 54 to its distal end 56. The locking disc 18 further has a radial bore 64 which extends normal to and communicates with the axial bore 62. Bore 64 has a tapped inner surface 66 which receives the threaded shank 68a of a set screw 68. The set screw 68 can be advanced into the tapped bore 64 until its end 70 engages the outer surface of the introducing needle 12 to secure the introducing needle 12 to the locking disc 18.

Referring to FIGS. 1 and 8, the stabilized aspiration biopsy needle assembly 10 is used in the following manner. The introducing needle 12 is inserted percutaneously into the body and advanced through the target tissue 80 as illustrated in FIG. 8A. Indicia (not shown) may be provided on the outer surface of the introducing needle 12, such as in 5 mm increments to indicate depth of insertion. The locking disc 18 is placed about the shaft of the needle 12 prior to its insertion. Then, the trocar member 14 is inserted into the introducing needle 12 and advanced until the handle 38 formed at its proximal end 30 is received in the horizontal portion 24a of the slot 24 in the hub 22 of the introducing needle 12. At such position, the distal tip of the trocar member 14 will extend beyond the distal tip of the introducing needle 12 as illustrated in FIG. 8B because the trocar member 14 is longer than the introducing needle 12. The trocar member 14 is locked to the introducing needle 12 upon rotation about its axis, clockwise, downward as viewed in FIG. 1, to move the handle 38 into the vertical portion 24b of slot 24, until the handle 38 is in the position illustrated in FIG. 1.

Then, the coaxial unit, including the introducing needle 12 and the trocar member 14 secured thereto, is retracted so that the distal tip 22 of the introducing needle 12 is just in or at the lesion to be aspirated or biopsied as illustrated in FIG. 8C. However, the trocar member 14 remains embedded in the tissue sample. The locking disc 18 is then advanced to engage the skin 20 of the body and the set screw 68 is tightened. The handle 38 of trocar member 14 which depends from the shank portion 33 at the bottom thereof does not interfere with access to the cannula of the introducing needle 12 or the trough defined by the trocar member 14, permitting insertion of the aspiration needle axially through the open proximal ends of the trocar member 14 and introducing needle 12.

Then, the aspiration needle 16 is introduced through the introducing needle 12 along side the trocar member 14 until its distal tip 46 is advanced out of the distal end of the introducing needle into the tissue to be sampled as illustrated in FIG. 8D. Because the aspiration needle is of a smaller gauge than the trocar member, the aspiration needle 16 will not interfere with the trocar and will move freely therewithin with the trocar member defining a channel for the advancement of the aspiration needle. Also, because the outer surface of the semi-cylindrical trocar member conforms to the inner surface of the introducing needle, the residual lumen of the combined coaxial unit is maximized. When advanced to the target tissue, the aspiration needle may be manipulated drawing it in and out using short strokes to agitate the tissue or body fluids in the target area. The distance the trocar member 14 protrudes beyond the introducing needle 12 may vary depending on the application. Also, although in the exemplary illustration of use, the introducing needle is advanced into or through target tissue, the introducing needle may be advanced to the target area and the trocar member advanced into the target area as a function of application. The trocar member 14 provides a footed anchor for the distal end of the needle assembly 10, stabilizing the assembly to prevent lateral movement the distal end of the assembly during the manipulation of the aspiration needle 16.

In some situations, as in the placement of preoperative guides to direct a surgeon to non-palpable breast lesions, or other lesions, foreign bodies, or other normal structures within the body or organ of the body, the introducing needle 12 may be reintroduced back through the lesion. The trocar member 14 permits this by acting as a guide over which the introducing needle can pass back through the lesion. The introducing needle 12 may then be retained as a guide, or a wire guide may be introduced through the introducing needle.

I claim:

1. A method for locating and positioning an aspiration biopsy needle including an introducing needle, a trocar member and an aspiration needle, each having a distal end, in a target area within a human or veterinary body, comprising:
   inserting the introducing needle percutaneously into the body and advancing the introducing needle to the target area;
   stabilizing the distal end of the introducing needle against lateral movement relative to the target area by advancing the trocar member axially through the introducing needle until its distal end extends beyond the distal end of the introducing needle and at least into the target area to maintain the distal end of the introducing needle in line with the target area and to form a coaxial unit,
   introducing the aspiration needle axially into said coaxial unit formed by the trocar member and the introducing needle and advancing the aspiration needle through the coaxial unit formed by the trocar member and the introducing needle to the target area with the trocar member guiding the aspiration needle to the target area.

2. The method according to claim 1 wherein the trocar member is generally semi-cylindrical in shape over substantially its entire length.

3. The method according to claim 1 wherein the outer surface of the trocar member conforms to the inner surface of the introducing needle.

4. The method according to claim 1 which includes retracting the positioned needles relative to the target area until the distal end of the introducing needle is withdrawn out of the target area while said distal tip of the trocar member remains within said target area.

5. The method according to claim 4 which includes securing the trocar member to the introducing needle prior to retracting the positioned needles relative to the target area.

6. The method according to claim 4 which includes the step of supporting said coaxial unit relative to the exterior of the body.

7. The method according to claim 4 which includes the step of withdrawing the aspiration needle from the assembled unit and re-advancing the introducing needle into the target tissue to facilitate advancement of a guide wire to the target area.

8. A method for locating and positioning an aspiration biopsy needle, including an introducing needle, a trocar member and an aspiration needle, each having a distal end, in a target area within a human or veterinary body, comprising:
   inserting the introducing needle percutaneously into the body and advancing the introducing needle to locate its distal end in the target area;
   stabilizing the distal end of the introducing needle against lateral movement relative to the target area by advancing the trocar member axially through the introducing needle until its distal end extends beyond the distal end of the introducing needle to maintain the distal end of the introducing needle in line with the target area and to form a coaxial unit, retracting the coaxial unit formed by the positioned needles relative to the target area until the distal end of the introducing needle is withdrawn out of the target area while said distal end of said trocar member remains within said target area thereby preventing lateral movement of the introducing needle relative to the target area; and introducing the aspiration needle axially into the coaxial unit formed by the trocar member and the introducing needle and advancing the aspiration needle through the coaxial unit formed by the trocar member and the introducing needle to the target area with the trocar member guiding the aspiration needle to the target area.

9. A method for locating and positioning an aspiration biopsy needle including an introducing needle, a trocar member and an aspiration needle, each having a distal end, in a target area within a human or veterinary body, comprising:

inserting an introducing needle percutaneously into the body and advancing the introducing needle to locate its distal end in the target area;

verifying the positioning of the distal end of the introducing needle relative to the target area;

stabilizing the distal end of the introducing needle against lateral movement relative to the target area by advancing the trocar member axially through the introducing needle until its distal end extends beyond the distal end of the introducing needle to maintain the distal end of the introducing needle in line with the target area and to form a coaxial unit, securing the trocar member to the introducing needle to prevent relative axial movement between the trocar member and the introducing needle during a biopsy procedure;

retracting the coaxial unit formed by the positioned needles relative to the target area until the distal end of the introducing needle is withdrawn out of the target area while said distal end of said trocar member remains within said target area thereby preventing lateral movement of the introducing needle relative to the target area; and introducing the aspiration needle axially into the coaxial unit formed by the trocar member and the introducing needle and advancing the aspiration needle through the coaxial trocar member and introducing needle to the target area with the trocar member guiding the aspiration needle to the target area.

10. The method according to claim 9 wherein the trocar member is generally semi-cylindrical in shape over substantially its entire length.

11. The method according to claim 10 wherein the outer surface of the trocar member conforms to the inner surface of the introducing needle.

12. An aspiration biopsy needle assembly for use in performing aspiration biopsy procedures at a target area within a human or veterinary body, said needle assembly comprising:

an introducing needle having a shaft portion with a proximal end and a distal end, said introducing needle being adapted for introduction percutaneously into the body and to be advanced therewithin to the target area;

a trocar member having a proximal end and a distal end, said trocar member being adapted for insertion and advancement axially through said introducing needle until its distal end extends beyond the distal end of said introducing needle and at least into the target area to form a coaxial unit with said distal end of said trocar member located within said target area;

securing means for securing said trocar member to said introducing needle to prevent relative axial movement between said trocar member and said introducing needle during an aspiration biopsy procedure whereby said trocar member stabilizes the distal end of the introducing needle against lateral movement relative to the target area, and an aspiration needle adapted for insertion into said coaxial unit formed by said trocar member and said introducing needle and to be advanced axially therewithin along side said trocar member and through introducing needle to the target area with said trocar member guiding said aspiration needle to the target area.

13. The needle assembly according to claim 12 wherein said trocar member is generally semi-cylindrical in shape over substantially its entire length.

14. The needle assembly according to claim 12 wherein the outer surface of said trocar member conforms to the inner surface of said introducing needle.

15. The needle assembly according to claim 12 including support means engaging the body at the point of entry of said introducing needle for supporting said coaxial unit exterior of the body.

16. The needle assembly according to claim 15 wherein said support means comprises a locking disc constructed and arranged for receiving and locking to said shaft portion of said introducing needle and defining a support surface engaging the body.

17. The needle assembly according to claim 12 wherein said securing means comprises an extension portion on the proximal end of said trocar member, and a guide channel in said hub of said introducing needle for receiving said extension portion.

18. An aspiration biopsy needle assembly for use in performing aspiration biopsy procedures at a target area within a human or veterinary body, said needle assembly comprising: p1 an introducing needle having a proximal end and a distal end, said introducing needle being adapted for introduction percutaneously into the body and to be advanced therewithin to locate its distal end in the target area;

a trocar member having a proximal end and a distal end, said trocar member being adapted for insertion and advancement axially through said introducing needle until its distal end extends beyond the distal end of said introducing needle to form a coaxial unit, securing means for securing said trocar member to said introducing needle to prevent relative axial movement between said trocar member and said introducing needle during an aspiration biopsy procedure whereby when said introducing needle is retracted relative to the target tissue until the distal end of the introducing needle is withdrawn out of the target tissue, said distal end of said trocar member remains within said target area and prevents lateral movement of said distal end of said introducing needle relative to said target area; and an aspiration needle adapted for insertion into said coaxial unit formed by said trocar member and said introducing needle and to be advanced axially therewithin along side said trocar member and through said introducing needle to the target area with said trocar member guiding said aspiration needle to the target area.

19. In an aspiration biopsy needle assembly for use in performing aspiration of body fluid or tissue in a target area within a human or veterinary body, including an introducing needle adapted for introduction into the body and advancement therewithin to locate its distal end in a target area and an aspiration needle adapted to be advanced axially through the introducing needle to the target area, the improvement comprising:

a trocar member having a distal end, said trocar member being adapted for advancement axially through the introducing needle prior to introduction of the aspiration needle into the introducing needle, until said distal end of said trocar member extends beyond the distal end of the introducing needle thereby stabilizing the distal end of the introducing needle; and means for securing the trocar member to the introducing needle to prevent relative axial movement between said trocar member and the introducing needle, whereby if the introducing needle is retracted relative to the target area until the distal end of the introducing needle is withdrawn out of the target tissue, said distal end of said trocar member remains in the target area to stabilize the distal end of said introducing needle relative to the target area, maintaining the distal end of the introducing needle in line with the target area, and said trocar member defining a guide channel for receiving the aspiration needle and guiding the aspiration needle to the target area.

* * * * *

UNITED STATES PATENT AND TRADEMARK OFFICE
CERTIFICATE OF CORRECTION

PATENT NO. : 5,057,085
DATED : October 15, 1991
INVENTOR(S) : Daniel B. Kopans

It is certified that error appears in the above-identified patent and that said Letters Patent is hereby corrected as shown below:

Column 3, line 26 delete "(".

Column 8, line 44, delete "pl".

Signed and Sealed this

Second Day of March, 1993

*Attest:*

STEPHEN G. KUNIN

*Attesting Officer*   *Acting Commissioner of Patents and Trademarks*